(12) United States Patent
Durham et al.

(10) Patent No.: US 8,771,753 B2
(45) Date of Patent: Jul. 8, 2014

(54) SYSTEMS AND METHODS FOR GENERATING GERMICIDAL COMPOSITIONS

(71) Applicants: Carmine J. Durham, Middleton, WI (US); R. Andrew Morgan, Middleton, WI (US); Michael C. Pawlak, Middleton, WI (US)

(72) Inventors: Carmine J. Durham, Middleton, WI (US); R. Andrew Morgan, Middleton, WI (US); Michael C. Pawlak, Middleton, WI (US)

(73) Assignee: Zurex Pharmagra, LLC, Middleton, WI (US)

(*) Notice: Subject to any disclaimer, the term of this patent is extended or adjusted under 35 U.S.C. 154(b) by 0 days.

(21) Appl. No.: 13/621,645

(22) Filed: Sep. 17, 2012

(65) Prior Publication Data

US 2013/0071492 A1 Mar. 21, 2013

Related U.S. Application Data

(60) Provisional application No. 61/535,829, filed on Sep. 16, 2011, provisional application No. 61/598,153, filed on Feb. 13, 2012.

(51) Int. Cl.
*A01N 59/08* (2006.01)
*A01N 59/00* (2006.01)

(52) U.S. Cl.
CPC ..................................... *A01N 59/00* (2013.01)
USPC ......... 424/661; 210/143; 210/192; 210/195.1

(58) Field of Classification Search
None
See application file for complete search history.

(56) References Cited

U.S. PATENT DOCUMENTS

| | | | | |
|---|---|---|---|---|
| 3,873,438 A * | 3/1975 | Anderson et al. | ............. | 204/268 |
| 4,062,743 A * | 12/1977 | Ahn et al. | ..................... | 205/512 |
| 4,082,630 A * | 4/1978 | Wiley et al. | ................... | 205/537 |
| 5,084,149 A * | 1/1992 | Kaczur et al. | ................. | 205/556 |
| 5,958,229 A * | 9/1999 | Filiopoulos et al. | .......... | 210/206 |
| 6,126,810 A * | 10/2000 | Fricker et al. | ................. | 205/500 |
| 6,719,891 B2 * | 4/2004 | Ruhr et al. | ..................... | 205/500 |
| 6,921,743 B2 * | 7/2005 | Scheper et al. | ............... | 510/220 |
| 7,323,118 B2 * | 1/2008 | Calderon | ................. | 252/187.32 |
| 7,651,704 B2 * | 1/2010 | Hinze | ......................... | 424/616 |
| 8,394,253 B2 * | 3/2013 | Peters et al. | ................. | 205/499 |
| 2004/0055896 A1 | 3/2004 | Anderson | | |
| 2004/0062818 A1 * | 4/2004 | Calderon | ...................... | 424/661 |
| 2006/0096618 A1 * | 5/2006 | Price et al. | ................... | 134/25.2 |
| 2006/0144718 A1 * | 7/2006 | Lambie | ......................... | 205/701 |
| 2007/0138020 A1 | 6/2007 | Balagopal | | |
| 2008/0008621 A1 | 1/2008 | Ikeda | | |
| 2008/0200355 A1 * | 8/2008 | Emmons | ....................... | 507/269 |
| 2010/0116688 A1 * | 5/2010 | Irani | ............................ | 205/742 |
| 2010/0183745 A1 | 7/2010 | Rossi | | |
| 2010/0307757 A1 * | 12/2010 | Blow et al. | ................. | 166/308.2 |
| 2011/0186462 A1 * | 8/2011 | Storey et al. | ............... | 206/524.1 |
| 2012/0055778 A1 * | 3/2012 | Schehr | ........................... | 203/10 |
| 2012/0061251 A1 * | 3/2012 | Von Broembsen | ........... | 205/349 |
| 2012/0291800 A1 * | 11/2012 | Johnson et al. | ................ | 134/3 |

OTHER PUBLICATIONS

Lenntech: Electrolytic process for chlorine and caustic soda (posted on internet on Feb. 21, 2006).*
Lenntech. Electrolytic Processes for Chlorine and Caustic Soda. Lentech.com available online Feb. 21, 2006.*
International Search Report mailed Mar. 4, 2013 from International Patent Application No. PCT/US2012/055778.

* cited by examiner

*Primary Examiner* — Frederick Krass
*Assistant Examiner* — Olga V Tcherkasskaya
(74) *Attorney, Agent, or Firm* — Casimir Jones SC

(57) ABSTRACT

The present invention relates to systems and methods for generating germicidal compositions for use in a wide variety of settings, including agricultural settings, food production settings, hospitality settings, health care settings, health club settings, exercise facility settings, research based settings, veterinarian settings, medical settings, hydraulic fracturing settings, and/or any setting requiring disinfection.

16 Claims, 2 Drawing Sheets

SYSTEMS AND METHODS FOR GENERATING GERMICIDAL COMPOSITIONS

FIELD OF THE INVENTION

The present invention relates to systems and methods for generating germicidal compositions for use in a wide variety of settings, including agricultural settings, food production settings, hospitality settings, health care settings, health club settings, exercise facility settings, research based settings, veterinarian settings, medical settings, hydraulic fracturing settings, and/or any setting requiring disinfection.

BACKGROUND

Today's consumer demands that the product they are provided be of the highest quality and safe to eat or drink. The production and processing of safe, nutritional, high quality milk and food starts on the farm. As farms get larger their ability to defend and control their operations against pest and harmful micro-organisms becomes even more critical. Pure water, animal and premise hygiene are indispensable in a well-managed operation (e.g., agricultural setting).

Improved and more comprehensive on-farm hygiene tools leading to a safe and wholesome agriculturally-based products (e.g., milk and food products) and healthy animals for the generation of such products are needed.

SUMMARY OF THE INVENTION

The present invention relates to systems and methods for generating germicidal compositions for use in a wide variety of settings, including agricultural settings, food production settings, hospitality settings, health care settings, health club settings, exercise facility settings, research based settings, veterinarian settings, medical settings, hydraulic fracturing settings, and/or any setting requiring disinfection.

The systems and methods of the present invention provide new levels of hygiene protection, providing solutions created on-site, with superior germicidal efficacy at a fraction of the cost of current germicidal alternatives. For example, the systems and methods of the present invention provide the ability to create a concentrated germicidal solution, to be used in a multitude of on-farm applications, at a fraction of the cost of common disinfectants. Moreover, the present invention provides compositions configured for specific disinfectant purposes.

Accordingly, in certain embodiments, the present invention provides systems comprising a sodium chloride solution, water, an electrolytic cell, and at least one chamber wherein the electrolytic cell is configured to a) receive the sodium chloride solution mixed with the water, b) remove hydrogen from the sodium chloride solution mixed with the water, and c) generate a germicidal composition and wherein the chamber is configured to receive the germicidal composition generated with the electrolytic cell.

The systems are not limited to a particular manner of generating the germicidal composition. In some embodiments, the germicidal composition is generated through removal of hydrogen from the sodium chloride solution mixed with the water. In some embodiments, the electrolytic cell is configured to generate the germicidal composition comprising a combination of chlorine, hypochlorite, hypochlorous acid and chlorine dioxide.

In some embodiments, the germicidal composition is measured in parts per million (PPM) of free available chlorine (FAC). The combination of chlorines (e.g., a combination of chlorine, hypochlorite, hypochlorous acid and chlorine dioxide) has been proven to be many times more effective than common chlorine bleach (sodium hypochlorite), and is safe when applied on skin tissue. In some embodiments, the PPM of FAC in a germicidal composition can be modified to meet the needs of a wide range of dairy sizes and desired uses/needs. In some embodiments, the system and methods of the present invention are capable of generating germicidal composition at any desired amount and/or concentration (e.g., in an amount from 125,000 PPM of FAC up to 25,000,000 PPM of FAC within a 24 hour production period) (e.g., in a range from 1,440,000 PPM of FAC (e.g., 180 gallons of 8,000 PPM of FAC) up to 4,800,000 PPM of FAC within a 24 hour production period)).

The systems of the present invention are not limited to use within a particular setting. Indeed, in some embodiments, the systems may be used in facility settings (e.g., external sanitation; flooring sanitation; equipment sanitation; vehicle sanitation; etc.), food settings (e.g., food preparation settings; animal eating settings; storage of food settings), water treatment settings, and/or animal hygiene settings.

In some embodiments, the system further comprises two or more additional agents, wherein the two or more additional agents are stored in a manner permitting combination of a generated germicidal composition with any combination (e.g., via blending/mixing) of two or more of the additional agents.

The present invention is not limited to a particular manner of combination of the germicidal composition and the two or more additional agents. In some embodiments, the combination is configured to occur automatically. In some embodiments, the system is configured to provide any programmed amount of the two or more additional agents for purposes of combination.

The present invention is not limited to particular additional agents. Examples of an additional agent includes, but is not limited to, water, a detergent polymer (e.g., Acusol), a surfactant (e.g., tomadol ethoxylate) (e.g. an ionic surfactant) (e.g. a non-ionic surfactant) (e.g., a cationic quarternary ammonion compound (e.g., cetylpyridinium chloride (e.g., Ammonyx)) (e.g., alkyl dimethyl benzylammonium chloride (e.g., BTC-835)) (e.g., an amphoteric surfactant (e.g., KDC-3) (e.g., amphoteric LH)), a hydrotope (e.g., sodium xylene sulfonate), a dye (e.g., tartrazine (dye keyacid tart yellow)) (e.g., blue dye) (e.g., green grams), citric acid, an emollient (e.g., propylene glycol) (e.g., urea), a sequestration agent (e.g., chelating agent (e.g., versene 100/sequestrene 30A)) (e.g., potassium hydroxide (e.g., caustic potash)) (e.g., sodium hydroxide (e.g., caustic soda)) (e.g., magnesium hydroxide (e.g., flogel)), an odorant (e.g., perfume), a mineral acid (e.g., Videt A-85), and a medicinal agent for animal hygiene, facility hygiene, general sanitization, disinfection and water treatment preparation purposes.

In some embodiments, the system generates a combination of a germicidal composition and water, a detergent polymer (e.g., Acusol), a surfactant (e.g., tomadol ethoxylate) (e.g, an ionic surfactant) (e.g., a non-ionic surfactant) (e.g., a cationic quarternary ammonion compound (e.g., cetylpyridinium chloride (e.g., Ammonyx)) (e.g., alkyl dimethyl benzylammonium chloride (e.g., BTC-835)) (e.g., an amphoteric surfactant (e.g., KDC-3) (e.g., amphoteric LH)), a hydrotope (e.g., sodium xylene sulfonate), and a dye (e.g., tartrazine (dye keyacid tart yellow)) (e.g., blue dye) (e.g., green grams). In some embodiments, such a combination is configured for pre-milking udder preparation purposes.

In some embodiments, the system generates a combination of a germicidal composition and water, a detergent polymer (e.g., Acusol), citric acid, a surfactant (e.g., tomadol ethoxylate) (e.g, an ionic surfactant) (e.g., a non-ionic surfactant) (e.g., a cationic quarternary ammonion compound (e.g., cetylpyridinium chloride (e.g., Ammonyx)) (e.g., alkyl dimethyl benzylammonium chloride (e.g., BTC-835)) (e.g., an amphoteric surfactant (e.g., KDC-3) (e.g., amphoteric LH)), an emollient (e.g., propylene glycol) (e.g., urea), a sequestration agent (e.g., chelating agent (e.g., versene 100/sequestrene 30A)) (e.g., potassium hydroxide (e.g., caustic potash)) (e.g., sodium hydroxide (e.g., caustic soda)) (e.g., magnesium hydroxide (e.g., flogel)), and a dye (e.g., tartrazine (dye keyacid tart yellow)) (e.g., blue dye) (e.g., green grams). In some embodiments, such a combination is configured for post-milking teat purposes.

The present invention further provides post-milking teat solutions having a noticeable color when applied to a tissue (e.g., a teat) (e.g., blue, red, yellow, black, orange). In some embodiments, the color is configured to remain noticeable when applied to a tissue for an extended period of time (e.g., 1 minute, 10 minutes, 20 minutes, 1 hour, 6 hours, 12 hours, 1 day, etc.).

In some embodiments, the system generates a combination of a germicidal composition and water, a surfactant (e.g., tomadol ethoxylate) (e.g, an ionic surfactant) (e.g., a non-ionic surfactant) (e.g., a cationic quarternary ammonion compound (e.g., cetylpyridinium chloride (e.g., Ammonyx)) (e.g., alkyl dimethyl benzylammonium chloride (e.g., BTC-835)) (e.g., an amphoteric surfactant (e.g., KDC-3) (e.g., amphoteric LH)), a sequestration agent (e.g., chelating agent (e.g., versene 100/sequestrene 30A)) (e.g., potassium hydroxide (e.g., caustic potash)) (e.g., sodium hydroxide (e.g., caustic soda)) (e.g., magnesium hydroxide (e.g., flogel)), an odorant (e.g., perfume), and a dye (e.g., tartrazine (dye keyacid tart yellow)) (e.g., blue dye) (e.g., green grams). In some embodiments, such a combination is configured for laundry purposes.

In some embodiments, the system generates a combination of a germicidal composition and water, a sequestration agent (e.g., chelating agent (e.g., versene 100/sequestrene 30A)) (e.g., potassium hydroxide (e.g., caustic potash)) (e.g., sodium hydroxide (e.g., caustic soda)) (e.g., magnesium hydroxide (e.g., flogel)), and a detergent polymer (e.g., Acusol). In some embodiments, such a combination is configured for cleaning-in-place purposes.

In some embodiments, the system generates a combination of a germicidal composition and water, a detergent polymer (e.g., Acusol), a sequestration agent (e.g., chelating agent (e.g., versene 100/sequestrene 30A)) (e.g., potassium hydroxide (e.g., caustic potash)) (e.g., sodium hydroxide (e.g., caustic soda)) (e.g., magnesium hydroxide (e.g., flogel)), a hydrotope (e.g., sodium xylene sulfonate), a surfactant (e.g., tomadol ethoxylate) (e.g, an ionic surfactant) (e.g, an ionic surfactant) (e.g., a non-ionic surfactant) (e.g., a cationic quarternary ammonion compound (e.g., cetylpyridinium chloride (e.g., Ammonyx)) (e.g., alkyl dimethyl benzylammonium chloride (e.g., BTC-835)) (e.g., an amphoteric surfactant (e.g., KDC-3) (e.g., amphoteric LH)). In some embodiments, such a combination is configured for premise purposes.

In some embodiments, the system generates a combination of a germicidal composition and water, a surfactant (e.g., tomadol ethoxylate) (e.g, an ionic surfactant) (e.g., a non-ionic surfactant) (e.g., a cationic quarternary ammonion compound (e.g., cetylpyridinium chloride (e.g., Ammonyx)) (e.g., alkyl dimethyl benzylammonium chloride (e.g., BTC-835)) (e.g., an amphoteric surfactant (e.g., KDC-3) (e.g., amphoteric LH)), and a mineral acid (e.g., Videt A-85). In some embodiments, such a combination is configured for footbath purposes.

In some embodiments, the system generates a germicidal composition configured for use in hydraulic fracturing settings. The system is not limited to a particular hydraulic fracturing setting. In some embodiments, the hydraulic fracturing setting involves extraction of oil. In some embodiments, the hydraulic fracturing setting involves extraction of natural gas. The germicidal compositions are not limited to a particular use within a hydraulic fracturing setting. In some embodiments, the germicidal composition is used to inhibit and/or kill the growth of bacteria and/or microorganisms associated within a hydraulic fracturing setting. In some embodiments, the germicidal compositions are configured to prevent the bacteria and/or microorganisms from producing contaminate byproducts (e.g., gas). In some embodiments, the germicidal compositions are configured to prevent the bacteria and/or microorganisms from interfering with (e.g., breaking down) agents used in hydraulic fracturing (e.g., gelling agents) (e.g., fracturing fluid). In some embodiments, the germicidal compositions used to inhibit and/or kill the growth of bacteria and/or microorganisms associated within a hydraulic fracturing setting is combined with one or more additional agents. Examples of additional agents include, but are not limited to, water, a detergent polymer (e.g., Acusol), a surfactant (e.g., tomadol ethoxylate), cetylpyridinium chloride (e.g., Ammonyx), sodium xylene sulfonate, an amphoteric surfactant (e.g., KDC-3), a surfactant (e.g., tomadol ethoxylate) (e.g, an ionic surfactant) (e.g., a non-ionic surfactant) (e.g., a cationic quarternary ammonion compound (e.g., cetylpyridinium chloride (e.g., Ammonyx)) (e.g., alkyl dimethyl benzylammonium chloride (e.g., BTC-835)) (e.g., an amphoteric surfactant (e.g., KDC-3) (e.g., amphoteric LH)), a dye (e.g., tartrazine (dye keyacid tart yellow)), citric acid, an emollient (e.g., propylene glycol) (e.g., urea), blue dye, a sequestration agent (e.g., chelating agent (e.g., versene 100/sequestrene 30A)) (e.g., potassium hydroxide (e.g., caustic potash)) (e.g., sodium hydroxide (e.g., caustic soda)) (e.g., magnesium hydroxide (e.g., flogel)), an odorant (e.g., perfume), a dye (e.g., green grams), alkyl dimethyl benzylammonium chloride (e.g., BTC-835), a mineral acid (e.g., Videt A-85), and a medicinal agent. In some embodiments, the germicidal composition is co-administered with an additional bactericide and/or biocide (e.g., 2,2-Dibromo-3-nitrilopropionamide, polynuclear aromatic hydrocarbons, polycyclic organic matter, gluteraldehyde).

In some embodiments, the system is a closed system (e.g., for maintaining a sterile setting) (e.g., for maintaining a controlled setting).

In some embodiments, the systems further comprise a processor running an algorithm. In some embodiments, the algorithm is configured regulate the generation of the germicidal composition. In some embodiments, the algorithm is configured to regulate the combination of the germicidal composition with the two or more additional agents. In some embodiments, the algorithm is configured to present alerts regarding the system. Examples of such alerts include, but are not limited to, germicidal composition amount levels, time periods, identifications of used additional agents, system malfunctions, additional agent amount levels, sterility contaminations, amount levels of the germicidal composition combined with the additional agents.

In certain embodiments, the present invention provides methods for generating compositions comprising germicidal compositions combined with additional agents with such a system.

In certain embodiments, the present invention provides compositions generated with such systems and/or methods.

DETAILED DESCRIPTION

The systems and methods of the present invention are not limited to use and/or application within a particular setting. In some embodiments, the systems and methods of the present invention are used within an animal-based setting (e.g., agricultural, veterinarian, academic, research based, etc). In some embodiments, the systems and methods of the present invention are used within a hydraulic fracturing setting. In some embodiments, the systems and methods of the present invention are used within any setting requiring use and/or application of a disinfectant.

Figure 1:
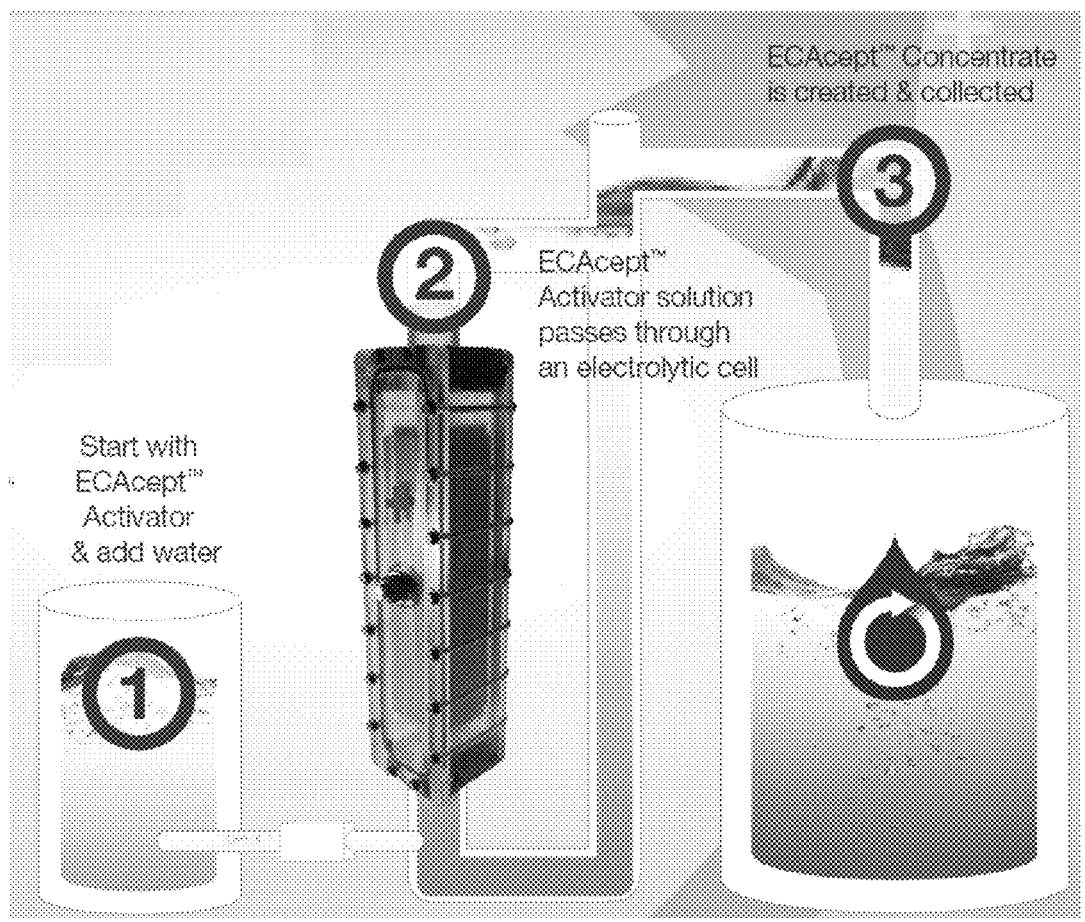
FIG. 1 depicts a process involving Electro-Chemical Activation, which involves the process of passing a sodium chloride solution, and treated water (1) through an electrolytic cell (2) in order to generate, by electro-chemical energy conversion, a germicidally active solution (3).

In particular, the present invention utilizes Electro-Chemical Activation (ECA). The present invention is not limited to particular technique or mechanism associated with ECA. In some embodiments, ECA involves the process of passing a sodium chloride solution, and treated water (1) through an electrolytic cell (2) in order to generate, by electro-chemical energy conversion, a germicidally active solution (3) (see, e.g., FIG. 1). Accordingly, the present invention provides devices, systems and methods utilizing ECA.

The present invention are not limited to a particular sodium chloride solution. In some embodiments, the sodium chloride solution is ECAcept Activator solution. The present invention is not limited to a particular ECAcept Activator solution. In some embodiments, the ECAcept Activator solution comprises an aqueous, purified sodium chloride solution. In some embodiments, the sodium chloride solution is a brine solution. The present invention is not limited to particular concentration and/or purification parameters for the sodium chloride solution.

The present invention is not limited to a particular electrolytic cell. In some embodiments, the electrolytic cell is configured to efficiently and reliably generate chlorine from a base solution (e.g., a base solution comprising a sodium chloride solution). In some embodiments, the electrolytic cell is configured to liberate hydrogen from a base solution (e.g., a base solution comprising a sodium chloride solution). In some embodiments, the electrolytic cell is configured for passive and/or active hydrogen removal. In some embodiments, the electrolytic cell is configured for high velocity electrolyte flow, sodium chloride solution conductivity control, full wave D.C. rectification, recirculating cell loop, and/or no cell electrode penetrations. In some embodiments, the electrolytic cell is configured to generate a solution comprising chlorine, hypochlorite, hypochlorous acid and chlorine dioxide from a sodium chloride solution. In some embodiments, the electrolytic cell is as described or similar to the electrolytic cells described in U.S. Pat. No. 7,897,022, U.S. patent application Ser. Nos. 13/026,947 and 13/026,939; each of which are herein incorporated by reference in their entireties.

The present invention is not limited to a particular germicidally active solution. In some embodiments, the germicidally active solution is ECAcept Concentrate. The systems and methods of the present invention are not limited to a particular ECAcept Concentrate. In some embodiments, the ECAcept Concentrate solution is, for example, a combination of chlorine, hypochlorite, hypochlorous acid and chlorine dioxide.

Accordingly, the present invention provides compositions comprising ECAcept Concentrate. The ECAcept Concentrate is not limited to particular measurement and/or concentration parameters. In some embodiments, the ECAcept Concentrate is measured in parts per million (PPM) of free available chlorine (FAC). The combination of chlorines has been proven to be many times more effective than common chlorine bleach (sodium hypochlorite), and is safe when applied on skin tissue. In some embodiments, the PPM of FAC in a ECAcept Concentrate can be modified to meet the needs of a wide range of dairy sizes and desired uses/needs. In some embodiments, the system and methods of the present invention are capable of generating ECAcept Concentrate at any desired amount and/or concentration (e.g., in an amount from 125,000 PPM of FAC up to 25,000,000 PPM of FAC within a 24 hour production period) (e.g., in a range from 1,440,000 PPM of FAC (e.g., 180 gallons of 8,000 PPM of FAC) up to 4,800,000 PPM of FAC within a 24 hour production period).

The ECAcept Concentrate is not limited to a particular use or function. In some embodiments, the ECAcept Concentrate is a powerful disinfectant. Indeed, experiments conducted during the course of developing embodiments for the present invention demonstrated that generated ECAcept Concentrate is 10 times more efficient at the same dilution rate at killing harmful micro-organisms than standard commercial bleach (e.g., 5.25%-12.5% sodium hypochlorite), without having caustic, corrosive, skin harming characteristics. The ECAcept Concentrate is not limited to particular disinfectant uses. In some embodiments, the ECAcept Concentrate is used for animal hygiene disinfectant purposes. For example, in some embodiments, the ECAcept Concentrate is used for pre and/or post milking hygiene purposes. For example, in some embodiments, the ECAcept Concentrate is used for hoof treatment. In some embodiments, the ECAcept Concentrate is used for premise hygiene purposes. For example, in some embodiments, the ECAcept Concentrate is used for cleaning, disinfecting, and/or sanitizing the structural premise (e.g., the exterior walls, platforms, etc). In some embodiments, the ECAcept Concentrate is used for equipment cleaning, disinfecting, and/or sanitizing. In some embodiments, the ECAcept Concentrate is used for cleaning, disinfecting, and/or sanitizing the calf hutches, treatment, and/or hospital areas. In some embodiments, the ECAcept Concentrate is used for cleaning, disinfecting, and/or sanitizing the cleaning-in-place (CIP) locations. In some embodiments, the ECAcept Concentrate is used for cleaning, disinfecting, and/or sanitizing the laundry locations. In some embodiments, the ECAcept Concentrate is used for water treatment. For example, in some embodiments, the ECAcept Concentrate is used for iron and/or manganese remediation from a water source. In some embodiments, the ECAcept Concentrate is used for biofilm removal from a water source. In some embodiments, the ECAcept Concentrate is used for disinfecting a water source. In some embodiments, the ECAcept Concentrate is generated with a relatively neutral pH so as to keep the solution safe for skin contact (e.g., contact with cow teats and skin tissue).

In some embodiments, following its generation, the ECAcept Concentrate is further modified for enhanced purposes and/or uses. The present invention is not limited to a particular manner of modifying the ECAcept Concentrate. In some embodiments, the ECAcept Concentrate is further modified through combination with additional agents.

For example, in some embodiments, pre-milking udder preparation solutions are generated by combining the ECAcept Concentrate with additional agents. The present invention is not limited to particular agents. In some embodiments, a pre-milking udder preparation solution is generated by combining the ECAcept Concentrate with, for example, one or more of water, a detergent polymer (e.g., Acusol), a surfactant (e.g., tomadol ethoxylate) (e.g, an ionic surfactant) (e.g., a non-ionic surfactant) (e.g., a cationic quarternary ammonion compound (e.g., cetylpyridinium chloride (e.g., Ammonyx)) (e.g., alkyl dimethyl benzylammonium chloride (e.g., BTC-835)) (e.g., an amphoteric surfactant (e.g., KDC-3) (e.g., amphoteric LH)), a hydrotope (e.g., sodium xylene sulfonate), and a dye (e.g., tartrazine (dye keyacid tart yellow)) (e.g., blue dye) (e.g., green grams). In some embodiments, the pre-milking udder preparation solution further comprises an emollient (e.g., propylene glycol) (e.g., urea). The pre-milking udder preparation solutions are not limited to particular ingredient parameters (e.g., amounts relative to other ingredients, concentrations, pH levels, dilution amounts, etc.).

In some embodiments, post-milking teat solutions are generated by combining the ECAcept Concentrate with additional agents. The present invention is not limited to particular agents. In some embodiments, the post-milking teat solution is generated by combining the ECAcept Concentrate with, for example, one or more of water, a detergent polymer (e.g., Acusol), citric acid, a surfactant (e.g., tomadol ethoxylate) (e.g, an ionic surfactant) (e.g., a non-ionic surfactant) (e.g., a cationic quarternary ammonion compound (e.g., cetylpyridinium chloride (e.g., Ammonyx)) (e.g., alkyl dimethyl benzylammonium chloride (e.g., BTC-835)) (e.g., an amphoteric surfactant (e.g., KDC-3) (e.g., amphoteric LH)), an emollient (e.g., propylene glycol) (e.g., urea), a sequestration agent (e.g., chelating agent (e.g., versene 100/sequestrene 30A)) (e.g., potassium hydroxide (e.g., caustic potash)) (e.g., sodium hydroxide (e.g., caustic soda)) (e.g., magnesium hydroxide (e.g., flogel)), and a dye (e.g., tartrazine (dye keyacid tart yellow)) (e.g., blue dye) (e.g., green grams). In some embodiments, the post-milking teat solution further comprises a polyvinyl alcohol (e.g., celvol 205-S). The post-milking teat solutions are not limited to particular ingredient parameters (e.g., amounts relative to other ingredients, concentrations, pH levels, dilution amounts, etc.).

In some embodiments, laundry solutions are generated by combining the ECAcept Concentrate with additional agents. The present invention is not limited to particular agents. In some embodiments, the laundry solutions are generated by combining the ECAcept Concentrate with, for example, one or more of water, a surfactant (e.g., tomadol ethoxylate) (e.g, an ionic surfactant) (e.g., a non-ionic surfactant) (e.g., a cationic quarternary ammonion compound (e.g., cetylpyridinium chloride (e.g., Ammonyx)) (e.g., alkyl dimethyl benzylammonium chloride (e.g., BTC-835)) (e.g., an amphoteric surfactant (e.g., KDC-3) (e.g., amphoteric LH)), a sequestration agent (e.g., chelating agent (e.g., versene 100/sequestrene 30A)) (e.g., potassium hydroxide (e.g., caustic potash)) (e.g., sodium hydroxide (e.g., caustic soda)) (e.g., magnesium hydroxide (e.g., flogel)), an odorant (e.g., perfume), and a dye (e.g., tartrazine (dye keyacid tart yellow)) (e.g., blue dye) (e.g., green grams). The laundry solutions are not limited to particular ingredient parameters (e.g., amounts relative to other ingredients, concentrations, pH levels, dilution amounts, etc.).

In some embodiments, cleaning-in-place (CIP) solutions are generated by combining the ECAcept Concentrate with additional agents. The present invention is not limited to particular agents. In some embodiments, the cleaning-in-place solutions are generated by combining the ECAcept Concentrate with, for example, one or more of water, a sequestration agent (e.g., chelating agent (e.g., versene 100/sequestrene 30A)) (e.g., potassium hydroxide (e.g., caustic potash)) (e.g., sodium hydroxide (e.g., caustic soda)) (e.g., magnesium hydroxide (e.g., flogel)), and a detergent polymer (e.g., Acusol). The cleaning-in-place solutions are not limited to particular ingredient parameters (e.g., amounts relative to other ingredients, concentrations, pH levels, dilution amounts, etc.).

In some embodiments, premise solutions are generated by combining the ECAcept Concentrate with additional agents. The present invention is not limited to particular agents. In some embodiments, the premise solutions are generated by combining the ECAcept Concentrate with, for example, one or more of water, a detergent polymer (e.g., Acusol), a sequestration agent (e.g., chelating agent (e.g., versene 100/sequestrene 30A)) (e.g., potassium hydroxide (e.g., caustic potash)) (e.g., sodium hydroxide (e.g., caustic soda)) (e.g., magnesium hydroxide (e.g., flogel)), a hydrotope (e.g., sodium xylene sulfonate), a surfactant (e.g., tomadol ethoxylate) (e.g, an ionic surfactant) (e.g., a non-ionic surfactant) (e.g., a cationic quarternary ammonion compound (e.g., cetylpyridinium chloride (e.g., Ammonyx)) (e.g., alkyl dimethyl benzylammonium chloride (e.g., BTC-835)) (e.g., an amphoteric surfactant (e.g., KDC-3) (e.g., amphoteric LH)). The premise solutions are not limited to particular ingredient parameters (e.g., amounts relative to other ingredients, concentrations, pH levels, dilution amounts, etc.).

In some embodiments, footbath solutions are generated by combining the ECAcept Concentrate with additional agents. The present invention is not limited to particular agents. In some embodiments, the footbath solutions are generated by combining the ECAcept Concentrate with, for example, one or more of water, a surfactant (e.g., tomadol ethoxylate) (e.g, an ionic surfactant) (e.g., a non-ionic surfactant) (e.g., a cationic quarternary ammonion compound (e.g., cetylpyridinium chloride (e.g., Ammonyx)) (e.g., alkyl dimethyl benzylammonium chloride (e.g., BTC-835)) (e.g., an amphoteric surfactant (e.g., KDC-3) (e.g., amphoteric LH)), and a mineral acid (e.g., Videt A-85). The footbath solutions are not limited to particular ingredient parameters (e.g., amounts relative to other ingredients, concentrations, pH levels, dilution amounts, etc.).

In some embodiments, medicinal solutions are generated by combining the ECAcept Concentrate with additional agents. In some embodiments, the medicinal solutions are configured for topical application. In some embodiments, the medicinal solutions are configured for oral administration. In some embodiments, the medicinal solutions are configured for intravenous administration. The present invention is not limited to particular agents. In some embodiments, the medicinal solutions are generated by combining the ECAcept Concentrate with, for example, one or more agents designed to prevent and/or treat a medical condition (e.g., anti-biotic agents, anti-microbial agents, sedating agents, analgesic agents, specific medical condition treatment agents (e.g., agents designed to treat and/or prevent mastitis) (e.g., agents designed to treat and/or prevent conditions associated with mucosal and non-mucosal tissue) (e.g., agents designed to treat and/or prevent pink eye, tissue rash) (e.g., agents designed to treat and/or prevent conditions associated with wounds), growth inducing agents (e.g., hormones), vitamins, etc.).

Figure 2:
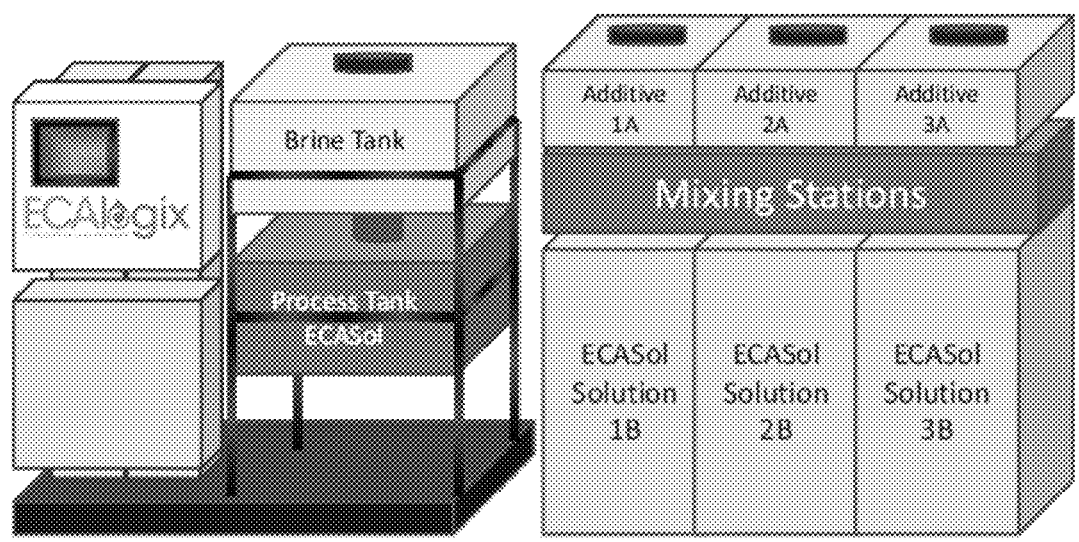
FIG. 2 shows a system for generating ECAcept Concentrate (see, e.g., Brine Tank and Process Tank), and combining it with additional agents (see, e.g., Additive 1A, Additive 2A, and Additive 3A) via the mixing station to create modified EACcept Concentrate (see, e.g., 1B, 2B, 3B).

The present invention is not limited to a particular technique for combining the ECAcept Concentrate with additional agents. In some embodiments, the additional agents are stored within a system/device that generates the ECAcept Concentrate. For example, FIG. 2 shows a system for generating ECAcept Concentrate (see, e.g., Brine Tank and Process Tank), and combining it with additional agents (see, e.g., Additive 1A, Additive 2A, and Additive 3A) via the mixing station to create modified EACcept Concentrate (see, e.g., 1B, 2B, 3B) (e.g., a pre-milking udder preparation solution; a post-milking teat solution; a laundry solution; a cleaning-in-place solution; a premise solution; a footbath solution). In some embodiments, the additional agents are stored within a system/device that generates the ECAcept Concentrate in a manner that permits combination with generated ECAcept Concentrate in a closed setting (e.g., thereby maintaining a controlled and/or a sterile setting) (e.g., the system shown in FIG. 2). In some embodiments, the additional agents are stored in a manner compatible with RFID technology (e.g., the additional agent container if flagged with an RFID tag) and the system is has RFID tags. In some such embodiments, the systems are configured to operate only if the RFID tags match in a desired manner (e.g., additional agents stored in a manner not having RFID tag matching with the system RFID tag results in non-system operation). In some embodiments, the system is configured such that generation of ECAcept Concentrate and combination with additional agents occurs within the same setting (e.g., the same location). In some embodiments, the system is configured such that generation of ECAcept Concentrate and combination with additional agents occurs at different locations. In some embodiments, generation of a modified ECAcept Concentrate (e.g., a pre-milking udder preparation solution; a post-milking teat solution; a laundry solution; a cleaning-in-place solution; a premise solution; a footbath solution) is controlled by a user prior to generation of ECAcept Concentrate. In some embodiments, generation of a modified ECAcept Concentrate (e.g., a pre-milking udder preparation solution; a post-milking teat solution; a laundry solution; a cleaning-in-place solution; a premise solution; a footbath solution) is controlled by a user following generation of ECAcept Concentrate. In some embodiments, generation of a modified ECAcept Concentrate is physically accomplished by a user. In some embodiments, generation of a modified ECAcept Concentrate is occurs automatically (e.g., user-free).

The present invention provides systems configured to generate ECAcept Concentrate and/or modified ECAcept Concentrate (e.g., a pre-milking udder preparation solution; a post-milking teat solution; a laundry solution; a cleaning-in-place solution; a premise solution; a footbath solution). In some embodiments, the system comprises a sodium chloride solution, water, an electrolytic cell, and chamber for collecting/storing generated ECAcept Concentrate. In some embodiments, the system comprises a sodium chloride solution, water, an electrolytic cell, additional agents for generating modified ECAcept Concentrate, and chamber for collecting/storing generated ECAcept Concentrate and/or modified ECAcept Concentrate. In some embodiments, all aspects of the system are controllable by a user. For example, the amount of ECAcept Concentrate and/or modified ECAcept Concentrate (e.g., over a period of time) may be controlled, the particular concentrations (e.g., PPM of FAC) may be controlled. In addition, the amount of additional agents to use when generating modified ECAcept Concentrate (e.g., a pre-milking udder preparation solution; a post-milking teat solution; a laundry solution; a cleaning-in-place solution; a premise solution; a footbath solution) may be controlled so as to generate a precisely desired end product. In addition, in some embodiments, the system has a processor (e.g., a computer interface) (e.g., an algorithm) for facilitating such control. In some embodiments, the processor is compatible with html5 or higher format. In some embodiments, the system may be controlled either on-site or off-site (e.g., via wireless (e.g., wi-fi) interaction). In some embodiments, the system may be controlled via an application (e.g., a downloadable phone application). In some embodiments, the system is configured to present data to a user (e.g., concentration levels of particular ECAcept Concentrate solutions and/or modified ECAcept Concentrate solutions) (e.g., amounts of particular ECAcept Concentrate solutions and/or modified ECAcept Concentrate solutions) (e.g., warnings as to particular ECAcept Concentrate solutions and/or modified ECAcept Concentrate solutions (e.g., warnings that amounts are too high or low)) (e.g., sterility contaminations). In some embodiments, the systems may be programmable to automatically generate desired ECAcept Concentrate and/or modified ECAcept Concentrate solutions (e.g., programmed to automatically generate more solution upon the occurrence of certain events (e.g., stored amounts reaching particular levels, elapsing of a particular time-span, etc.)). In some embodiments, the systems are configured to monitor the generation of ECAcept Concentrate and/or modified ECAcept concentrate to ensure proper generation according to programmed parameters and/or to ensure quality control. The systems are further configured to store generated ECAcept Concentrate and/or modified ECAcept Concentrate in a controlled and/or sterile manner, in any desired amount, for any extended amount of time. The systems are further configured to store generated ECAcept Concentrate and/or modified ECAcept Concentrate in a tightly controlled manner, in any desired amount, for any extended amount of time. The systems are further configured to store multiple solutions of ECAcept Concentrate, modified ECAcept Concentrate, and/or additional agents at any given time. The systems are further configured to dispense generated ECAcept Concentrate and/or modified ECAcept Concentrate in a controlled and/or sterile manner, in any desired amount, for any extended amount of time. The systems are further configured to dispense generated ECAcept Concentrate and/or modified ECAcept Concentrate in a tightly controlled manner, in any desired amount, for any extended amount of time. The present invention provides methods for generating ECAcept Concentrate and/or modified ECAcept Concentrate (e.g., a pre-milking udder preparation solution; a post-milking teat solution; a laundry solution; a cleaning-in-place solution; a premise solution; a footbath solution) with such a system.

In some embodiments, the system generates a germicidal composition configured for use in hydraulic fracturing settings. The system is not limited to a particular hydraulic fracturing setting. In some embodiments, the hydraulic fracturing setting involves extraction of oil. In some embodiments, the hydraulic fracturing setting involves extraction of natural gas. Hydraulic fracturing is used to, for example, increase or restore the rate at which fluids, such as petroleum, water, or natural gas can be produced from subterranean natural reservoirs. Reservoirs are typically, for example, porous sandstones, limestones or dolomite rocks, but also include 'unconventional reservoirs' such as shale rock or coal beds. Hydraulic fracturing enables the production of natural gas and oil from rock formations deep below the earth's surface (generally 5,000-20,000 feet (1,500-6,100 m)). At such depth, there may not be sufficient permeability or reservoir pressure to allow natural gas and oil to flow from the rock into the wellbore at economic rates. Thus, creating conductive fractures in the rock is essential to extract gas from shale reservoirs because of the extremely low natural permeability of shale. Fractures provide a conductive path connecting a larger area of the reservoir to the well, thereby increasing the area from which natural gas and liquids can be recovered from the targeted formation.

Problems associated with efficient hydraulic fracturing yields include, for example, bacteria and microorganisms that produce contaminant gas, break down gelling agents, and reduce the viscosity of fracturing fluid. In order to overcome such problems, the present invention provides germicidal compositions used to inhibit and/or kill the growth of bacteria and/or microorganisms associated within a hydraulic fracturing setting. In some embodiments, the germicidal compositions are configured to prevent the bacteria and/or microorganisms from producing contaminate byproducts (e.g., gas). In some embodiments, the germicidal compositions are configured to prevent the bacteria and/or microorganisms from interfering with (e.g., breaking down) agents used in hydraulic fracturing (e.g., gelling agents) (e.g., fracturing fluid). In some embodiments, the germicidal compositions used to inhibit and/or kill the growth of bacteria and/or microorganisms associated within a hydraulic fracturing setting is combined with one or more additional agents. Examples of additional agents include, but are not limited to, water, a detergent polymer (e.g., Acusol), a surfactant (e.g., tomadol ethoxylate) (e.g, an ionic surfactant) (e.g., a non-ionic surfactant) (e.g., a cationic quarternary ammonion compound (e.g., cetylpyridinium chloride (e.g., Ammonyx)) (e.g., alkyl dimethyl benzylammonium chloride (e.g., BTC-835)) (e.g., an amphoteric surfactant (e.g., KDC-3) (e.g., amphoteric LH)), cetylpyridinium chloride (e.g., Ammonyx), sodium xylene sulfonate, a dye (e.g., tartrazine (dye keyacid tart yellow)), citric acid, an emollient (e.g., propylene glycol) (e.g., urea), blue dye, a sequestration agent (e.g., chelating agent (e.g., versene 100/sequestrene 30A)) (e.g., potassium hydroxide (e.g., caustic potash)) (e.g., sodium hydroxide (e.g., caustic soda)) (e.g., magnesium hydroxide (e.g., flogel)), an odorant (e.g., perfume), a dye (e.g., green grams), sodium xylene sulfonate, alkyl dimethyl benzylammonium chloride (e.g., BTC-835), a mineral acid (e.g., Videt A-85), and a medicinal agent. In some embodiments, the germicidal composition is co-administered with an additional bactericide and/or biocide (e.g., 2,2-Dibromo-3-nitrilopropionamide, polynuclear aromatic hydrocarbons, polycyclic organic matter, gluteraldehyde).

Incorporation By Reference

The entire disclosure of each of the patent documents and scientific articles referred to herein is incorporated by reference for all purposes.

Equivalents

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A system for on-site production of a germicidal composition, comprising a sodium chloride solution, an electrolytic cell, two or more additional agents, and at least one chamber, wherein
    a) the electrolytic cell is configured to
        i) receive the sodium chloride solution,
        ii) remove hydrogen from the sodium chloride solution, and
        iii) generate a concentrate;
    b) the at least one chamber is configured to receive the concentrate generated with the electrolytic cell;
    c) the system is configured to automatically combine the two or more additional agents with the concentrate to produce the germicidal composition, wherein the two or more additional agents are selected from the group consisting of a detergent polymer, a surfactant, a hydrotrope, a dye, citric acid, an emollient, a sequestration agent, an odorant, a mineral acid, a medicinal agent, and water; and
    d) the system is closed.

2. The system of claim 1, wherein the germicidal composition is removed from the system following production.

3. The system of claim 2, wherein the germicidal composition is sterile.

4. The system of claim 1, wherein the two or more additional agents are a detergent polymer, a surfactant, a hydrotope, water and a dye.

5. The system of claim 4, wherein the germicidal composition is for pre-milking udder preparation cleaning.

6. The system of claim 1, wherein the two or more additional agents are a detergent polymer, citric acid, a surfactant, an emollient, a sequestration agent, water and a dye.

7. The system of claim 6, wherein the germicidal composition is for post-milking teat cleaning.

8. The system of claim 1, wherein the two or more additional agents are a surfactant, a sequestration agent, an odorant, water and a dye.

9. The system of claim 8, wherein germicidal composition is for laundry cleaning.

10. The system of claim 1, wherein the two or more additional agents are a sequestration agent, water and a detergent polymer.

11. The system of claim 10, wherein the germicidal composition is for cleaning-in-place.

12. The system of claim 1, wherein the two or more additional agents are a detergent polymer, sequestration agent, a hydrotope, water and a surfactant.

13. The system of claim 12, wherein germicidal composition is for premise cleaning.

14. The system of claim 1, wherein the two or more additional agents are a surfactant, water and a mineral acid.

15. The system of claim 14, wherein germicidal composition is for footbath cleaning.

16. The system of claim 1, further comprising two or more processors running two or more algorithms, wherein the one or more algorithms are a) configured to automatically regulate converting sodium chloride solution to a solution having chlorine, hypochlorite, hypochlorous acid, and chlorine dioxide, and/or b) configured to automatically regulate the adding or mixing of the two or more functional agents with the concentrate.

\* \* \* \* \*